(12) United States Patent
Feldman et al.

(10) Patent No.: US 10,076,669 B2
(45) Date of Patent: Sep. 18, 2018

(54) ADMITTANCE MEASUREMENT FOR TUNING BI-VENTRICULAR PACEMAKERS

(75) Inventors: Marc D. Feldman, San Antonio, TX (US); John Porterfield, Austin, TX (US); Erik Larson, Austin, TX (US); Jonathan W. Valvano, Austin, TX (US); John A. Pearce, Austin, TX (US)

(73) Assignees: Admittance Technologies, Inc., San Antonio, TX (US); Board of Regents, The University of Texas System, Austin, TX (US)

( * ) Notice: Subject to any disclaimer, the term of this patent is extended or adjusted under 35 U.S.C. 154(b) by 214 days.

(21) Appl. No.: 13/373,850

(22) Filed: Dec. 2, 2011

(65) Prior Publication Data

US 2012/0150252 A1    Jun. 14, 2012

Related U.S. Application Data

(60) Provisional application No. 61/459,280, filed on Dec. 10, 2010.

(51) Int. Cl.
*A61N 1/365* (2006.01)
*A61B 5/053* (2006.01)
*A61N 1/368* (2006.01)

(52) U.S. Cl.
CPC ........ *A61N 1/36571* (2013.01); *A61B 5/0538* (2013.01); *A61N 1/36521* (2013.01); *A61N 1/3682* (2013.01); *A61N 1/3684* (2013.01)

(58) Field of Classification Search
CPC .............. A61N 1/3682; A61N 1/36571; A61N 1/3684; A61N 1/36521; A61B 5/0538

(Continued)

(56) References Cited

U.S. PATENT DOCUMENTS

| | | | |
|---|---|---|---|
| 2004/0220637 A1* | 11/2004 | Zdeblick | A61B 5/02028 607/17 |
| 2009/0210020 A1* | 8/2009 | Feldman | A61B 5/0215 607/4 |

(Continued)

OTHER PUBLICATIONS

Zima, E., Lippert, M., Czygan, G, Merkely, G., "Determination of Left Ventricular Volume Changes by Intracardiac Conductance Using a Biventricular Electrode Configuration," the Eurpean Society of Cardiology, Europace, (vol. 8), (p. 537-544), (2006).

(Continued)

*Primary Examiner* — Alyssa M Alter
(74) *Attorney, Agent, or Firm* — Ansel M. Schwartz

(57) ABSTRACT

An apparatus for treating a heart of a patient includes a first lead and at least a second lead for pacing the heart adapted to be in electrical communication with the heart. The apparatus includes a microcontroller in communication with the first and second leads which triggers the first lead at either different times or the same time from when the microcontroller triggers the second lead. Alternatively, the apparatus includes a microcontroller in communication with the first and second leads that determines heart volume, including stroke volume, end-systolic volume, and calculated values including ejection fraction, from admittance from signals from the first and second leads and uses the admittance as feedback to control heart volume ejected, as measured by stroke volume, calculated values such as ejection fraction, and control end-systolic volume, with respect to the first and second leads. A method for treating the heart of a patient.

10 Claims, 5 Drawing Sheets

(58) Field of Classification Search
USPC .................................................... 607/18, 9
See application file for complete search history.

(56) References Cited

U.S. PATENT DOCUMENTS

2010/0004712 A1* 1/2010 Zhao et al. .................. 607/17
2011/0184301 A1* 7/2011 Holmstrom et al. ......... 600/516

OTHER PUBLICATIONS

Bocchiardo, M., Meyer Zu Vilsendorf, D., Militello, C., Lippert, M., Czygan, G., Gaita, F., Schauerte, P., Stellbrink, C., "Intracardiac Impedance Monitors Stroke Volume in Resynchronization Therapy Patients," European Society of Cardiology, Europace, (Feb. 25, 2010).

Bocchiardo, M., Meyer Zu Vilsendorf, D., Militello, C., Lippert, M., Czygan, G. Schauerte, P., Gaita, F., Stellbrink, C., "Resynchronization Therapy Optimization by Intracardiac Impedance," European Society of Cardiology, Europace, (vol. 12), (p. 1589-1595), (2010).

* cited by examiner

US 10,076,669 B2

ADMITTANCE MEASUREMENT FOR TUNING BI-VENTRICULAR PACEMAKERS

CROSS-REFERENCE TO RELATED APPLICATIONS

This application claims priority from U.S. provisional patent application 61/459,280 filed on Dec. 10, 2010, which is incorporated by reference herein.

FIELD OF THE INVENTION

The present invention is related to pacing the heart. (As used herein, references to the "present invention" or "invention" relate to exemplary embodiments and not necessarily to every embodiment encompassed by the appended claims.) More specifically the present invention is related to pacing the heart by using admittance as feedback to control, such as maximize, heart volume ejected, as measured by stroke volume, and calculated values such as ejection fraction, and control, such as minimize, end-systolic volume, and/or triggering a first lead at different times from when a microcontroller triggers a second lead of a pacemaker.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Heart failure (HF) is one of the leading causes of admission to the hospital.[1] Studies have shown that patients with dilated hearts have a reduction in the frequency of hospital admission and prolongation of life with the implantation of bi-ventricular pacemakers and automatic implantable cardiac defibrillators (AICDs).[2-5] These benefits extend to the millions of patients with both ischemic and idiopathic cardiomyopathy. Recently, "piggybacking" technology onto AICDs and bi-ventricular pacemakers for sensing the progression of impending heart failure to reduce the number and length of stay of hospital admissions for CHF has been proposed.[6-14]

Currently, the only way to tell if cardiac output is being maximized by a timing algorithm (or using bi-ventricular pacing) is to use imaging methods such as echocardiography which require trips to the hospital, and trained physicians to both perform the measurements and interpret results. The body of literature shows that pacemaker timing optimization improves outcomes in patients, and that there would be immediate benefit for a new device, which performed this calibration automatically.

[1] Bordachar P, Garrigue S, Reuter S, Hocini M, Kobeissi A, Gaggini G, Jais P, Haissaguerre M, Clementy J, Hemodynamic assessment of right, left, and biventricular pacing by peak endocardial acceleration and echocardiography in patients with end-stage heart failure. Pacing Clin Electrophysiol 2000; 23:1726-1730.

[2] Bordachar P, Labrousse L, Ploux S, Thambo J B, Lafitte S, Reant P, Jais P, Haissaguerre M, Clementy J, Dos Santos P: Validation of a new noninvasive device for the monitoring of peak endocardial acceleration in pigs: implications for optimization of pacing site and configuration. J Cardiovasc Electrophysiol 2008; 19:725-729.

[3] Gorcsan J, 3rd, Abraham T, Agler D A, Bax J J, Derumeaux G, Grimm R A, Martin R, Steinberg J S, Sutton M S, Yu C M: Echocardiography for cardiac resynchronization therapy: recommendations for performance and reporting—a report from the American Society of Echocardiography Dyssynchrony Writing Group endorsed by the Heart Rhythm Society. J Am Soc Echocardiogr 2008; 21:191-213.

[4] Hasan A: How Should Echocardiography Be Used in CRT Optimization? J Am Soc Echocardiogr 2010; 23:867-871.

[5] Klimczak A, Chudzik M, Zielinska M, Budzikowski A S, Lewek J, J K W: Optimization of atrio-ventricular delay in patients with dual-chamber pacemaker. Int J Cardiol 2010; 141:222-226.

[6] Taha N, Zhang J, Ranjan R, Daneshvar S, Castillo E, Guillen E, Montoya M C, Velasquez G, Naqvi T Z: Biventricular pacemaker optimization guided by comprehensive echocardiography-preliminary observations regarding the effects on systolic and diastolic ventricular function and third heart sound. J Am Soc Echocardiogr 2010; 23:857-866.

[7] Kedia N, Ng K, Apperson-Hansen C, Wang C, Tchou P, Wilkoff B L, Grimm R A: Usefulness of atrioventricular delay optimization using Doppler assessment of mitral inflow in patients undergoing cardiac resynchronization therapy. Am J Cardiol 2006; 98:780-785.

The problem with constant rate pacemakers (and indeed adaptive pacing) is that the problem is not closed-loop. That is to say, there is no method for quantifying success continuously in pacing without the need for an expensive doctor visit. This invention will help to close the loop and provide the best possible pacing algorithm in both bi-v, and normal pacemakers, also allowing the device to self-calibrate for the first time.

The idea of multisite pacing has been shown to improve outcomes in patients receiving a multi-site pacing device. Additionally, optimization of multi-site pacing by maximizing stroke volume and ejection fraction, and minimizing end-systolic volume, has been shown to improve quality of life in patients using comprehensive echocardiography. However, proponents of this technology recognize that it is still too time, resource, and labor intensive. The new approach described in this invention will allow a measurement of real time stroke volume, end-systolic volume and ejection fraction coupled to existing bi-ventricular pacing leads already implanted within a patient. This new information will allow the use of a self-calibrating algorithm, which is simple, accurate, and shortens the doctor-patient interaction time. A self-calibrating pacemaker timing will outperform a one-time programmed pacemaker by requiring less trips to the doctor's office for calibration, saving the patient time and money, and also has the potential to perform better than a normal pacemaker, because it is tailored more closely to the patients needs.

Regarding alternative technologies which use electric fields, there are two which have been "piggybacked" onto bi-ventricular pacemakers and AICDs that have been tested in clinical trials. First, Chronicle® measures right heart pressures in an attempt to monitor increases that are indicative of heart failure.[6, 7, 9] Second, Optivol® and CorVue™ use lung conductance measurements as an indication of pulmonary edema.[8, 11, 12, 14] However, neither measures LV volume and thus they cannot be used to tune these pacing devices and maximize LV stroke volume and ejection fraction. More recently Stahl et al.[13, 15] have proposed generating an electric field in the RV, and detecting the fringe field from the LV bi-ventricular pacer lead. However, this measurement does not separate the lumped blood and myocardial components. Thus, there are currently no proposed technologies that can perform LV blood volume measurements.

BRIEF SUMMARY OF THE INVENTION

The present invention solves this problem by "piggybacking" an admittance measurement system onto bi-ventricular and AICD leads, and removing the myocardial contribution from the combined electrical blood/muscle signal to determine an increase in LV preload from baseline. Bi-ventricular and RV AICD leads are already located in ideal measurement locations—the lateral LV epicardium and the RV apex (FIG. 1a). Since blood has 5 times lower resistivity than myocardium, the preferential path for a substantial fraction of the current flow is the LV blood volume (FIG. 1b). The validity of the present approach was demonstrated by (a) deriving real-time LV blood conductance signals following instantaneous removal of the myocardial component of the signal utilizing epicardial electrodes, (b) detecting LV dilation with blood conductance in response to IV Neosynephrine comparable to the standard of endocardial crystals (see FIGS. 2 and 3), (c) detecting LV dilation with blood conductance in response to occlusion of the left anterior descending coronary artery, and (d) demonstrating that saline placed in the chest cavity to simulate a pleural effusion is not a source of artifact in the measurement of epicardial admittance.

The present invention pertains to an apparatus for treating a heart of a patient. The apparatus comprises a first lead and at least a second lead for pacing the heart adapted to be in electrical communication with the heart. The apparatus comprises a microcontroller in communication with the first and second leads which triggers the first lead at either different times or the same time from when the microcontroller triggers the second lead.

The present invention pertains to an apparatus for treating a heart of a patient. The apparatus comprises a first lead and at least a second lead for pacing the heart adapted to be in electrical communication with the heart. The apparatus comprises a microcontroller in communication with the first and second leads that determines heart volume, including stroke volume, end-systolic volume, and calculated values including ejection fraction, from admittance from signals from the first and second leads and uses the admittance as feedback to control heart volume ejected, as measured by stroke volume, calculated values such as ejection fraction, and control end-systolic volume, with respect to the first and second leads.

The present invention pertains to a method for treating a heart of a patient. The method comprises the steps of triggering with a microcontroller a first lead in electrical communication with the heart at various times for pacing the heart. There is the step of triggering with the microcontroller a second lead in electrical communication with the heart at different times than the various times for pacing the heart so that the microcontroller triggers the first lead at different times from when the microcontroller triggers the second lead.

The present invention pertains a method for treating the heart of a patient. The method comprises the steps of determining heart volume, including stroke volume, calculated values such as ejection fraction, and end-systolic volume, from admittance with a microcontroller from signals from a first lead and a second lead in electrical communication with the heart. There is the step of using the admittance as feedback to the microcontroller to control heart volume ejected, as measured by stroke volume, calculated values such as ejection fraction, and control end-systolic volume, with respect to the first and second leads.

BRIEF DESCRIPTION OF THE SEVERAL VIEWS OF THE DRAWING

In the accompanying drawings, the preferred embodiment of the invention and preferred methods of practicing the invention are illustrated in which.

DETAILED DESCRIPTION OF THE INVENTION

Figure 1A:
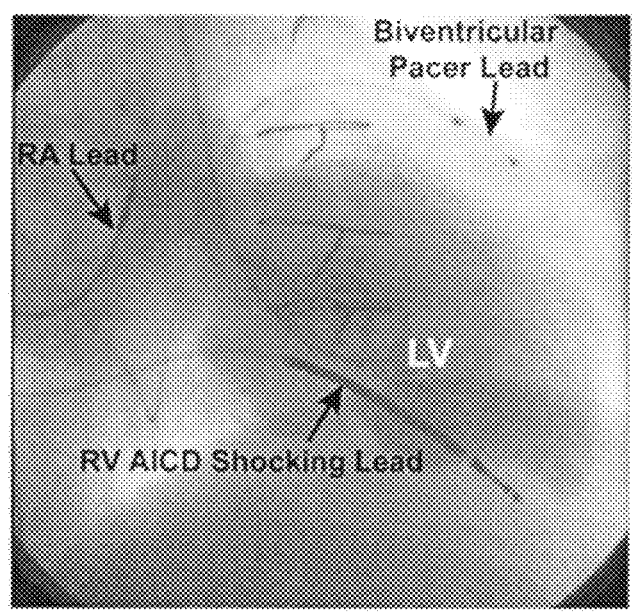
FIG. 1a shows a bi-plane left ventriculogram from a patient with CHF and a previously implanted AICD/bi-ventricular pacer demonstrating how the leads span the left ventricle (LV) blood from the RV apical septum to the lateral LV epicardium.
Figure 1B:
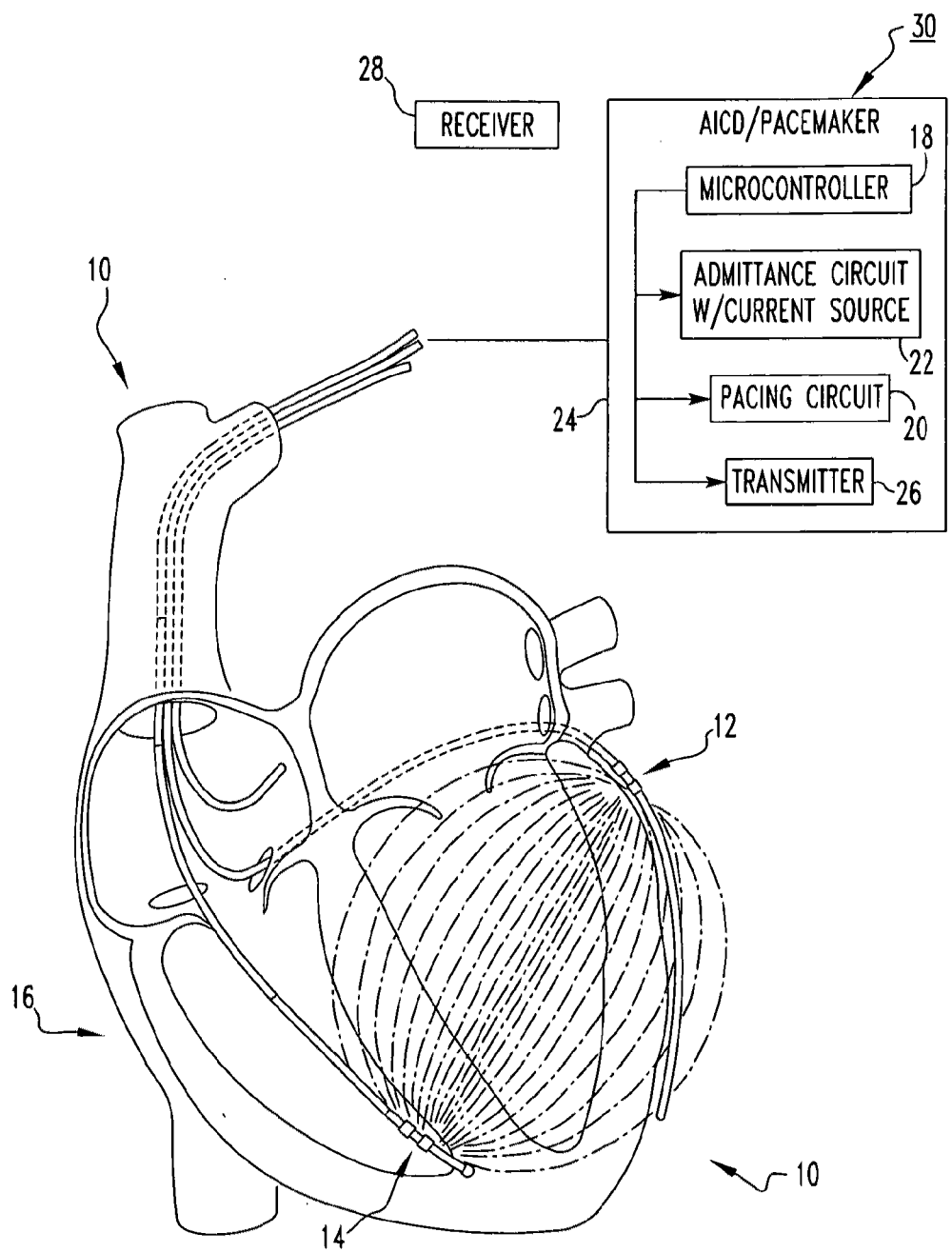
FIG. 1b shows the admittance electric field lines from the RV apical septum to the lateral LV epicardium regarding the apparatus of the present invention.
Figure 2:
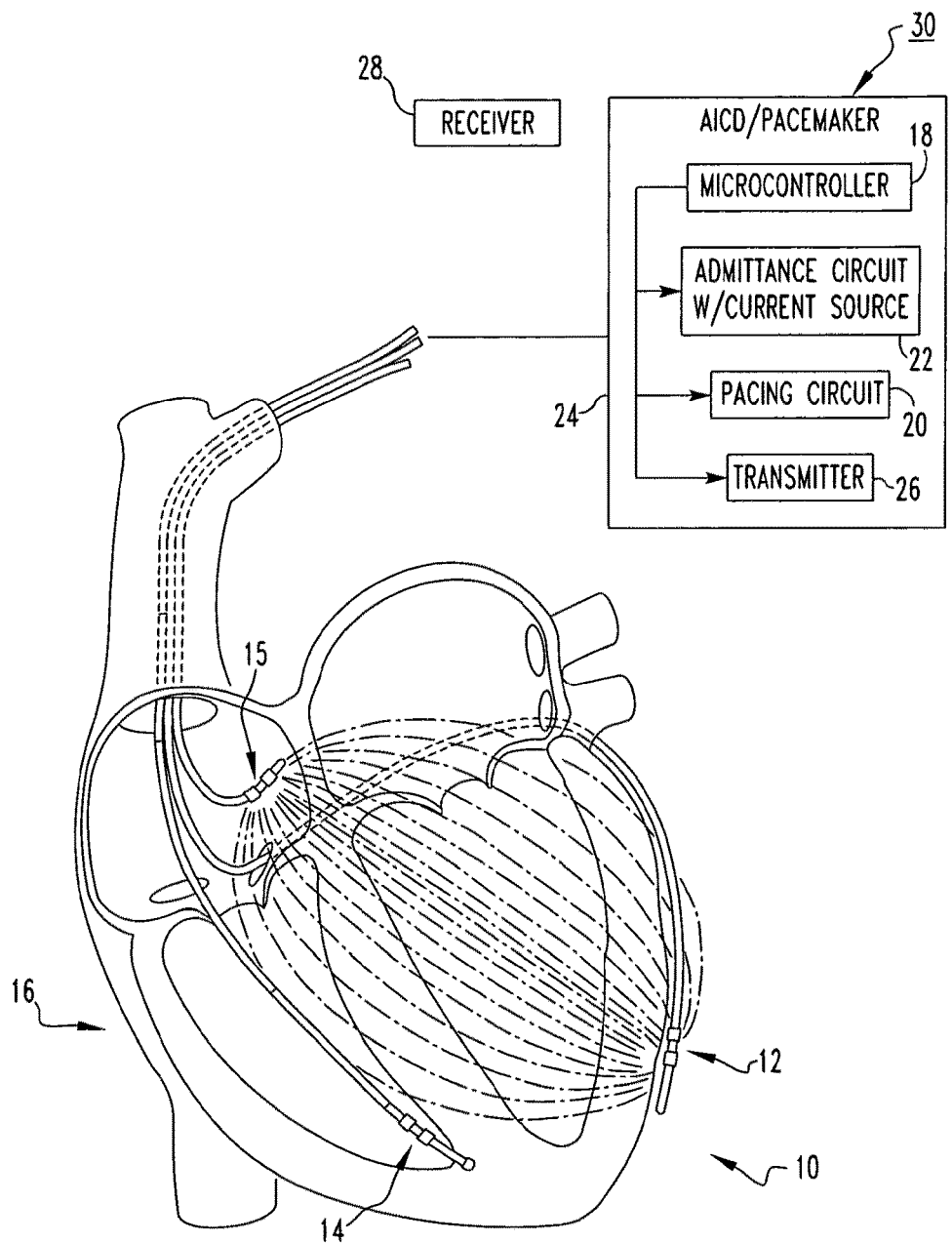
FIG. 2 shows a typical arrangement of three leads consisting of 2 electrodes each. This allows a normal pacemaker measurement to make 2 (or more) separate measurements of admittance across the heart.

Referring now to the drawings wherein like reference numerals refer to similar or identical parts throughout the several views, and more specifically to FIG. 1b thereof, there is shown an apparatus 10 for treating a heart 16 of a patient. The apparatus 10 comprises a first lead 12 and at least a second lead 14 for pacing the heart 16 adapted to be in electrical communication with the heart 16. The apparatus 10 comprises a microcontroller 18 in communication with the first and second leads 12, 14 which triggers the first lead 12 at either different times or the same time from when the microcontroller 18 triggers the second lead 14.

The apparatus 10 may include a pacing circuit 20 in communication with microcontroller 18 which receives a signal from the microcontroller 18 to activate the pacing circuit 20. The apparatus 10 may include an admittance circuit 22 which measures volume regarding the heart 16 in communication with the microcontroller 18. The microcontroller 18 controls when the admittance circuit 22 measures volume. The microcontroller 18 determines from the admittance circuit 22 whether stroke volume, ejection fraction and end-systolic volume regarding the heart 16 are increasing or decreasing over time, and changes the pacing circuit's operation to maximize the stroke volume and ejection fraction and to minimize the end-systolic volume.

The apparatus 10 may include a pacemaker 30 enclosure 24 and wherein the admittance circuit 22 is disposed in the pacemaker 30 enclosure 24. The microcontroller 18 may be disposed in the enclosure 24 and including a wireless transmitter 26 disposed in the enclosure 24 which transmits a condition signal indicating whether the heart's condition is getting worse, better or is without change. The pacing circuit 20 may pace each ventricle of the heart 16 separately, where each ventricle is paced separately using a variable time delay between a first and a second pace, or takes into account delay between atrial pacing and ventricular pacing, or a combination thereof. The apparatus may include at least a third lead 15 for multiple admittance measurements adapted to be in electrical communication with the heart.

The present invention pertains to an apparatus 10 for treating a heart 16 of a patient. The apparatus 10 comprises a first lead 12 and at least a second lead 14 for pacing the heart 16 adapted to be in electrical communication with the heart 16. The apparatus 10 comprises a microcontroller 18 in communication with the first and second leads 12, 14 that determines heart 16 volume, including stroke volume, end-systolic volume, and calculated values including ejection fraction, from admittance from signals from the first and second leads 12, 14 and uses the admittance as feedback to control heart 16 volume ejected, as measured by stroke volume, calculated values such as ejection fraction, and control end-systolic volume, with respect to the first and second leads 12, 14.

The present invention pertains to a method for treating a heart 16 of a patient. The method comprises the steps of triggering with a microcontroller 18 a first lead 12 in electrical communication with the heart 16 at various times for pacing the heart 16. There is the step of triggering with the microcontroller 18 a second lead 14 in electrical communication with the heart 16 at different times than the various times for pacing the heart 16 so that the microcontroller 18 triggers the first lead 12 at different times from when the microcontroller 18 triggers the second lead 14.

There may be the step of determining stroke volume, and systolic volume, and ejection fraction of the heart 16 using epicardial admittance. There may be the step of pacing the heart 16 by separately pacing each ventricle of the heart 16 using a variable time delay between a first and a second pace, or by taking into account delay between atrial pacing and ventricular pacing, or by a combination thereof. There may be the step of re-measuring stroke filing, and systolic volume, and ejection fraction after changing how the heart 16 is paced. There may be the step of comparing the determining step and the re-measuring step, and repeating them until the stroke volume and ejection fraction are maximal, and end-systolic volume is minimal.

The present invention pertains to a method for treating the heart 16 of a patient. The method comprises the steps of determining heart 16 volume, including stroke volume, calculated values such as ejection fraction, and end-systolic volume, from admittance with a microcontroller 18 from signals from a first lead 12 and a second lead 14 in electrical communication with the heart 16. There is the step of using the admittance as feedback to the microcontroller 18 to control heart 16 volume ejected, as measured by stroke volume, calculated values such as ejection fraction, and control end-systolic volume, with respect to the first and second leads 12, 14.

In the operation of the invention, the key elements of this invention include 1) the use of an epicardial admittance measurement to determine improvements in stroke volume and/or end systolic volume, and 2) the ability of this information to determine the best possible pacing algorithm to use based on which algorithm maximizes patient stroke volume, ejection fraction, and minimizes end-systolic volume from the first element.

The invention will determine which pacing algorithm maximizes patient stroke volume, ejection fraction, and minimizing end-systolic volume by cycling through each available timing algorithm (or by changing the timing between stimulation of each site in a multisite pacemaker 30) and measuring the LV volume, and derived stroke volume, end-systolic volume and ejection fraction for each. Maximizing the stroke volume in these situations will directly affect the ejection fraction of the patient, moving the patient into a higher functional NYHA class, and improving quality of life both immediately, and over time.

In regard to FIG. 1*b*, a pacemaker 30 (pacing) circuit is well known in the field, and little has been done to change its basic design since its invention. However, the method to control when the pacing circuit 20 fires varies with the type of technology. In the present invention, there are two main components: 1) a pacing circuit 20, and 2) a volume measurement (admittance) circuit. A microcontroller 18 will provide the signal to the pacing circuit 20 to control when each individual pacing site is activated. The microcontroller 18 will also control when the admittance circuit 22 measures volume. The microcontroller 18 will be able to determine from the admittance circuit 22 whether the stroke volume, ejection fraction and end-systolic volume are increasing or decreasing over time, and change the pacing algorithm to maximize the stroke volume and ejection fraction, and minimizing the end-systolic volume.

Further, the microcontroller 18 will signal process the results from the admittance circuit 22 within the pacemaker 30 enclosure, and then a signal indicating whether the patient condition is getting worse, better, or staying the same can be sent to the receiver 28 using the wireless transmitter 26. No extra processing will be necessary external to the implanted device, although, if desired, the processing of the data could occur outside of the patient in an alternative embodiment.

For 4 electrodes to measure admittance, only one processing circuit (admittance circuit 22 w/current source) is necessary. An additional embodiment of the current invention is for multiple admittance circuits to measure the volume of the LV from different locations, or for one admittance circuit to measure multiple locations in sequence. This redundancy can be used to increase accuracy in situations where implantation of the leads in their ideal locations is not possible.

Adaptive Pacing Algorithms

The key method for determining if a pacing algorithm is working correctly should be dependent on how effectively the heart 16 is pumping blood. Maximum effectiveness is therefore equivalent to maximum cardiac output.

Algorithm:
1. Determine stroke volume, end systolic volume, and ejection fraction using epicardial admittance.
2. Pace the heart 16 using either:
   a. A well known pacing method (see pacing "algorithm" method guide by Bernstein et al.; *Journal of Pacing and Clinical Electrophysiology*, Volume 25, No. 2, February 2002).
   b. A bi-ventricular pacing algorithm where each ventricle is paced separately using a variable time delay between the first and the second pace.
   c. A pacing method that takes into account delay between atrial pacing and ventricular pacing.
   d. Some combination of the above
3. Measure stroke volume, end systolic volume, and ejection fraction after changing algorithm.

4. Compare step 3 with step 1 and repeat 2-4 until the stroke volume and ejection fraction are maximal, and end-systolic volume is minimal.

Pacing methods (sometimes called "algorithms" by the medical community):
1. Well-known pacing algorithms such as those described in Bernstein et al. are often chosen for a patient at the time of implantation. However, there is no guarantee that the patient will not benefit from a changing pacing algorithm depending on their activity, long-term health status, or other factors. Switching between these well known pacing algorithms could provide both short-term benefit (such as when exercising), and long-term benefit (such as improved cardiac remodeling). Because the microcontroller 18 is in direct contact with the pacing unit, switching algorithms is a matter of outputting a different pacing pattern to the pacing unit. The specific event that will trigger a switch in pacing is dropping below an adaptive threshold for cardiac output. Over time, if the patient improves, the threshold for aggressive therapy may be changed. This adaptive nature of the threshold for treatment allows the pacer to adapt to changes that occur over a long time span. Cardiac output, stroke volume, ejection fraction and end-systolic volume are measured using the admittance system directly. Therefore, if cardiac output, stroke volume, and ejection fraction start to go down, at some threshold (much like Optivol from Medtronic), the pacing algorithm will be switched to maximize the cardiac output, stroke volume and ejection fraction again. Other currently deployed applications which do not use hemodynamic variables include accelerometers within the pacemaker 30 to determine that increased patient motion is present and hence higher demand is necessary for more rapid pacing.
2. It is possible to pace the heart 16 using leads in both the coronary veins (LV lead) and in the RV apex (RV lead). If the LV lead is paced separately from the RV lead, a nonzero time delay between the LV lead and the RV lead could produce a better cardiac output, stroke volume (SV), and ejection fraction (EF) than has been previously discussed using bi-ventricular pacing (such as Cardiac Resynchronization Therapy devices). Pacing separately is a matter of having multiple pacing circuits controlled by a microcontroller 18. There are already microcontrollers present within most current pacemakers. This measurement can be performed using a microcontroller 18 and multiple pacemakers, or multiple pacing circuits connected one per electrode.

Atrio-ventricular delay is often set at the time of pacemaker 30 implantation to maximize stroke volume and EF, and minimize end-systolic volume (ESV). This type of pacing is currently beneficial to the patient, but it requires a doctor's visit to change the timing delay between atria and ventricle. Real-time feedback from epicardial Admittance can address this problem in real time, like the previous two pacing methods. With the power of the feedback loop and a microcontroller 18 in the pacemaker 30, a doctor's visit will not be necessary. Doctors tune pacemakers using the same process outlined in the algorithm. They measure the volume of the heart 16 (usually using an echo machine), change the pacing algorithm (usually using the help of a clinical engineer), and they re-test the volume of the heart 16 (using another echo). The patient visit, doctor, and engineer are not necessary if the microcontroller 18 implanted within the pacemaker 30 makes these decisions in real time as the patient's heart 16 is changing volume over time. This will save, money, and time for all involved, reducing greatly the amount of time between the patient's onset of disease and treatment.

Figure 4:
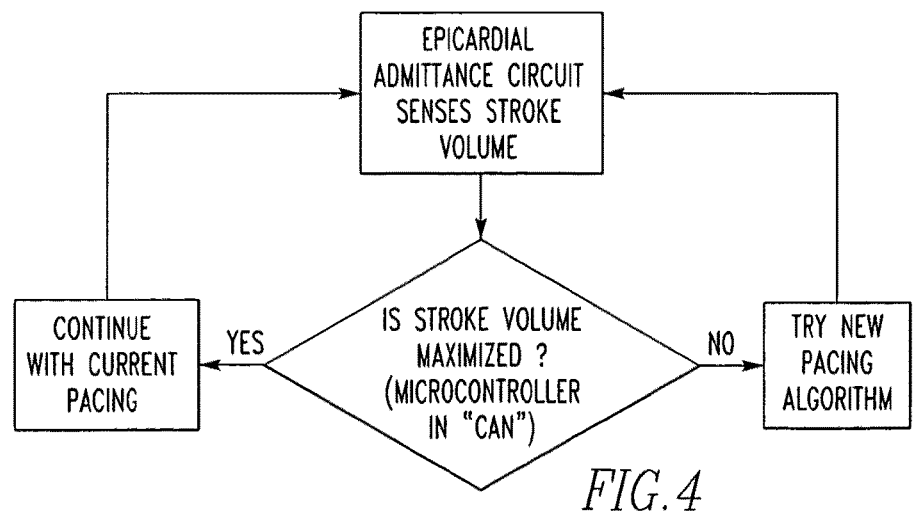
FIG. 4 is a flow chart of feedback loop of present invention.

What will be new and in the enclosure of the pacemaker 30 is:
1. Microcontroller 18 programming or an equivalent decision making circuit which provides feedback based on whether stroke volume and EF have been maximized, and ESV minimized. A variety of well known control algorithms can be used here, and their application is well known to one skilled in the art. The new feedback loop with the decision making process is shown in FIG. 4.
2. The admittance circuit 22, is described in U.S. patent application Ser. No. 12/657,832, incorporated by reference herein, but minimized to fit into the size of a pacemaker 30 enclosure. The miniaturization may be achieved by putting the entire admittance circuit 22 onto a chip if desired. See U.S. patent application Ser. No. 12/657,832, incorporated by reference herein. Such circuits can be made small enough without placement on a chip if desired.
3. An additional pacing circuit 20 is installed in the case where each lead in a bi-ventricular pacemaker 30 will be paced independently. This only mildly increases complexity. Basically, there would be 2 of the flow charts in parallel, delivering pacing pulses at different times. The end result and control algorithm are still the same.
4. Optionally, any known pacemaker configuration could benefit from this design, with various lead implant locations. However, nothing external to the pacemaker enclosure would need to change.

Calculation Theory and Epicardial Blood Conductance Measurement

Conductance measurements have been available as an invasive tool to detect instantaneous LV volume since 1981.[23] Tetrapolar electrodes are usually placed on a catheter located within the LV chamber to determine instantaneous volume by electrical conductance measurement. Conductance systems generate an electric field using a current source, and volume is determined from the instantaneous returning voltage signal. Conductance is the preferred measurement over resistance (or impedance) because it has a direct (not inverse) relationship with volume. Conductance electrodes have not been previously placed on the LV epicardium to interrogate the LV blood volume, as done in the current invention.

The relationship between measured blood conductance and LV blood volume is determined primarily by the shape of the current field in the blood pool and surrounding myocardium. For example, in a uniform electric field approximation the measured time-dependent resistance, $R_{blood}$, is proportional to the electrode separation distance, $L(t)$, and inversely proportional to the cross-sectional area of the field, $A(t)$; and the converse for the measured blood conductance, $G_{blood}$, where $\rho$ is blood resistivity:

$$R_{blood} = \frac{\rho L(t)}{A(t)}$$

$$G_{blood} = \frac{A(t)}{\rho L(t)}$$

Some of the measurement electrode positions will produce a blood conductance primarily sensitive to the cross-sectional area change while others are primarily sensitive to the separation distance. As the cross-sectional area of the LV increases, there is a corresponding increase in blood conductance. Thus, for the purposes of the current invention, area-dependent electrode configurations only were focused on.

Dynamic Muscle Conductance Removal

Epicardial admittance is a measurement taken in the complex plane, and has both a magnitude, |Y| (Siemens) and a phase, ∠Y (degrees). The values for admittance are a combination of both the muscle and blood conductance, and the muscle susceptance ($\omega C$), for both are present in the current field. The process for separating admittance into blood and muscle conductance was outlined previously for the case of a tetrapolar catheter where the blood and muscle are in parallel.[17] However, there is no previously proposed model for the separation of blood and muscle components of a cross-chamber epicardial admittance measurement, where the blood and muscle components are in series. This new theory to separate blood and muscle components is presented below.

$$R_m = \frac{-\text{Im}\{\vec{z}\} \times \left(1 + \left(\frac{\omega \epsilon_m}{\sigma_m}\right)^2\right)}{\frac{\omega \epsilon_m}{\sigma_m}}$$

$$R_b = \text{Re}\{\vec{z}\} - \frac{R_m}{1 + \left(\frac{\omega \epsilon_m}{\sigma_m}\right)^2}$$

Where $R_m$ is the resistance of muscle ($\Omega$), and $R_b$ is the resistance of blood ($\Omega$), $\epsilon_m$ is the permittivity of muscle (F/m), and $\sigma_n$ is the conductivity of muscle (S/m). The complex impedance $\vec{Z}$ can be separated into real ($\text{Re}\{\vec{Z}\}$) and imaginary parts ($\text{Im}\{\vec{Z}\}$). The properties of the myocardium $\sigma_n$, and $\epsilon_m$ can be calculated using a surface probe measurement.[17, 19] In an epicardial measurement the field generated is mostly transverse, while in a surface probe measurement (and in a traditional LV catheter measurement), the field is mostly longitudinal. This difference has been measured by others, and was corrected in the data by multiplying by a factor of 2.[24, 25] The penetration depth for the surface probe used to measure the porcine myocardial properties was 3.6 mm, which does not extend into the LV blood volume beneath.

LV Volume Measurement with 2 Dimensional Sonomicrometry

The standard of volume measurement used to validate this invention is two dimensional (2D) sonomicrometry (endocardial) crystals. 2D endocardial crystals is an acceptable alternative to 3D echocardiography in large animal hearts when the two short axes are equal in distance,[26-28] and this distance is maintained during acute LV dilation. Additionally, the porcine myocardium is prone to arrhythmias, and there is significant trauma associated with placing the third crystal plane through the septum. Consequently, 2D endocardial crystals are the practical approach. The two dimensions measured included the anterior-posterior and apex-base planes via pairs of 2 mm piezo-electric ultrasonic transducers positioned on the endocardial surface through a stab wound through the LV myocardium and secured with a purse-string suture. The two crystal pairs were attached to a digital sonomicrometer (Sonometrics Corporation, London, Ontario, Canada) and the digital output was then transformed into volume by fitting the points to a prolate ellipsoid.[26, 28]

Protocol

This invention was conducted in compliance with the United States Food and Drug Administration (FDA) Good Laboratory Practices Regulations (21 CFR Part 58), following approval of the animal use committee at the University of Texas Health Science Center San Antonio. For n=15 Yorkshire Pigs studied, the body weight ranged from 42 kg to 78 kg (mean=60±12.6 kg), 14 were male and 1 was female. Pigs were sedated with Telazol 4 mg/kg IM, intubated and anesthesia was maintained with 1-2% Isoflurane with 100% oxygen. The right neck was dissected to gain access to the jugular vein and carotid artery. A sternotomy was performed and the pericardium was partially opened. Amiodarone 150 mg IV was given over 30 min, and repeated 30 min later. Following loading of Amiodarone, a Lidocaine infusion was initiated at 1 µg/min for the remainder of the protocol. Although there was anticipated myocardial depression from this approach, there was greater concern that the porcine model has a low ventricular fibrillation threshold.

Instrumentation

Platinum-Platinum black electrodes were chosen for the experiment because of their low electrode interface impedance (Medtronic, Minneapolis, Minn.). Electrode locations were chosen to simulate the approximate positions of an RV AICD endocardial lead, and the bi-ventricular lead on the lateral LV epicardium. Two sets of 4 electrodes spaced 1 cm apart were sewn onto a felt backing, and each were sewn onto the LV epicardium. The anterior electrodes were sewn parallel to the distal LAD to simulate the RV AICD lead, and the posterior electrodes were sewn parallel to a left marginal vein to simulate the bi-ventricular lead. Electrode pairs were chosen for a cross-ventricular chamber tetrapolar measurement with a current producing and a voltage-sensing electrode on both the anterior and the posterior epicardium.

The pigs were also instrumented with two dimensional endocardial crystals as outlined above, a left carotid pressure sensor (3F, Scisense, London, ON), a 6F sheath in the jugular vein, an RV pressure sensor (inserted directly through the anterior RV wall (1.2 F, Scisense, London, ON), a descending thoracic saline filled balloon occluder (16 or 18 mm diameter, In Vivo Metric, Healdsburg, Calif.) to generate transient occlusion as an alternative method to produce LV dilation, and an aortic flow probe, which was placed in the descending thoracic aorta (Transonic, Ithaca, N.Y.) immediately distal to the balloon occluder to document that occlusion was obtained.

Properties Measurement and Hematocrit

An epicardial probe was applied to the surface of the intact beating open-chest heart. The stimulus current was generated using the instrumentation previously described.[29] Real-time $|\vec{Y}|$ and $\angle \vec{Y}$ were measured and myocardial permittivity ($\epsilon_m$) and conductivity ($\sigma_m$) were calculated as described previously.[19] Briefly, the surface probe "cell constant", k ($m^{-1}$), determined in saline of known electrical conductivity, is used to calculate: $\sigma_m = k \times G_m$ and $\epsilon_m = k \times C_m$, where $G_m = \text{Re}\{\vec{Y}\}$ and $C_m = \text{Im}\{\vec{Y}\}/\Omega$ and $\omega = 2\pi f$, where k is the cell constant of the probe used (1/m), $G_m$ is the conductance of muscle (S), $C_m$ is the capacitance of the muscle, and f is the frequency of excitation (Hz). Hematocrit was determined both at baseline and at the end of the experiment via capillary tubes and a Clay Adams Readacrit centrifuge (model CT-3400, Becton Dickinson, Sparks, Md.). Whole blood samples were spun for 5 minutes at 8,500 rpm, and the volume of packed red cells was expressed as a percentage of total volume.

Neosynephrine (Phenylephrine) for LV Dilatation

Neosynephrine was chosen to increase afterload and secondarily dilate the LV in a dose-response fashion to simulate LV dilation as would occur in a heart failure patient. Neosynephrine was infused at a constant rate of 75, 150, and 300 µg/min in the first n=2 pigs. For the later n=9 pigs, a lower dose of 37.5 µg/min was added to this same infusion protocol. Baseline and data from at least 2 doses of Neosynephrine where LV dilation occurred as defined by endocardial crystals, were required for data to be used in analysis. Some doses of Neosynephrine did not result in LV dilation and this varied in every pig. Thus, the doses given in the results section are the baseline, and mean low and high doses of Neosynephrine that achieved LV dilation. Each dose of Neosynephrine was infused for 10 minutes to achieve steady state, and then data were acquired over the subsequent 5 minutes for a total of 15 minutes per dose.

Data acquired included heart rate, carotid pressure (AoP), descending thoracic aortic flow (Ao Flow), short and long axis endocardial crystals, epicardial impedance magnitude ($|\vec{Z}|$) and phase angle ($\angle \vec{Z}$). Data were acquired while the respirator was suspended at end-expiration for at least 5 cardiac cycles.

Alternative Methods for LV Dilatation

To determine if LV dilation could be detected by epicardial admittance, two additional preparations were examined—acute LAD occlusion and transient aortic occlusion.

LAD Occlusion

A suture was placed under the middle LAD, proximal to the epicardial admittance electrodes, and tied off to produce an acute dilation of the middle and distal anterior myocardium. Data obtained were identical to the Neosynephrine protocol. Due to ventricular fibrillation, complete data were only obtained in n=6 porcine studies.

Transient Aortic Occlusion

Transient aortic occlusion was performed successfully in n=11 pigs. Occlusion was controlled by the introduction of saline into the occluder, and successful occlusion was defined by the reduction of descending thoracic aortic flow to less than 1 L/min. The flow probe was always immediately distal to the balloon occluder.

Pleural Effusion Simulation

Pleural effusions are common in heart failure patients, and are a common source of artifact in the measurement of lung conductance by systems such as Optivol™[8, 11, 14] and CorVue™, since the electrical fields generated by these devices extend into the lungs. Epicardial admittance generates an electric field, which extends across the LV and thus should not have this source of artifact. To test this hypothesis, the chest cavity was filled with saline during the measurement of LV epicardial admittance (both on the right and left sides of the heart). The pericardium was used as a sling to keep the saline from coming into direct contact with the electrodes, similar to the final implementation of epicardial admittance. Immediately after baseline measurements as outlined above, saline of conductivity close to blood (7941±124 µS/cm) was introduced into the chest. The introduced volume for n=7 pigs was 425±90 mL, and following introduction all measurements were repeated.

Data Analysis

The slope relating blood conductance (mS) and endocardial crystal volume (mL) was determined in 11 animals at up to three doses of Neosynephrine in each of up to 6 vectors, yielding a total of 99 paired measures of blood conductance and crystal volume (FIG. 3). Data were analyzed based on a repeated measures linear model with a compound symmetric autocorrelation matrix and fixed intercepts for each pig and vector. The significance of the relation between blood conductance and crystal volume was assessed using a Wald statistic for testing the null hypothesis that the coefficient of LV blood conductance in the repeated measures linear model is zero. Statistical testing was two-sided with a significance level of 5% using SAS Version 9.2 for Windows (SAS Institute, Cary, N.C.). For LAD occlusion, transient Ao occlusion, and pleural effusion simulation, paired baseline and intervention data were compared using a Student's t test, again with a level of significance of 5%. All results are reported as mean±standard deviation.

Results

Baseline Hemodynamics

The mean systolic aortic pressure was 80±13 mmHg, and the heart rate was 86±17 bpm. The mean LV end diastolic and end systolic long axis by crystals was 82±6 and 74±5 cm, respectively; and the mean LV end diastolic and end systolic short axis by crystals was 47±4 and 40±4 cm, respectively. The calculated mean LV EDV was 100±31 mL, and the mean LV ESV was 69±25 mL measured via endocardial crystals. The mean LVEF was 31±6%, consistent with a depressed but non-dilated LV preparation from the anesthetics and amiodarone given to minimize ventricular fibrillation. The mean descending thoracic flow was 8.0±1.8 L/min, and the mean RV systolic pressure was 19±3 mm Hg.

Hematocrit at the initiation of the protocol was 30.0±2.3%, and at the end of the protocol 33.0±4.7%, consistent with hemo-concentration due to minimal fluid administration during the protocol to mitigate changes in blood and myocardial electrical properties as a source of artifact. The mean distance from the LV apex to the most apical epicardial admittance electrode on the anterior surface was 3.0±0.9 cm, and on the posterior surface was 3.0±0.5 cm, consistent with the admittance electrodes being parallel to one another on either side of the LV epicardium.

The end diastolic and end systolic epicardial LV admittance magnitudes=$1/|\vec{Z}|$) were 15.8±2.0 and 14.5±1.9 mS, respectively; and the mean phase angles ($\angle \vec{Y}=-\angle \vec{Z}$) were 9.2±3.0 and 7.4±3.2 degrees, respectively.

Properties Summary

Myocardial properties were determined in each pig for use in the equations to separate the blood and muscle admittance as published previously.[19] The myocardial conductivity was $\tau_m$=0.33±0.03 S/m, the myocardial permittivity was $\varepsilon_m$=(19710±2786)*$\varepsilon_0$ F/m, and the calculated ratio of a/E for myocardium was 1,923,320±179,592 S/F.

Neosynephrine for LV Dilatation

Figure 3A:
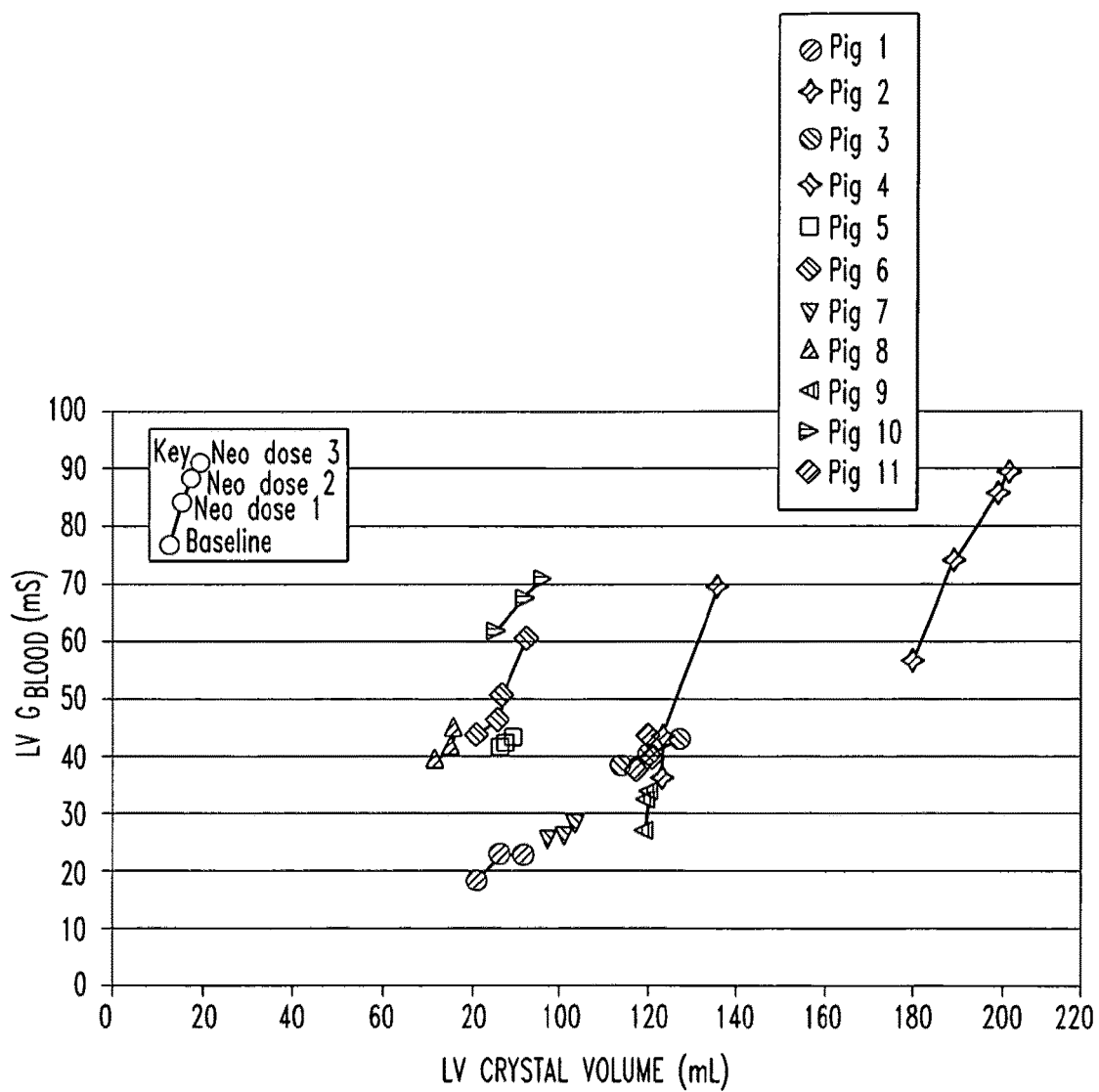
FIG. 3a shows the effect of Neosynephrine on LVEDV in Epicardial Lead Studies. Note that LV $G_{blood}$ tracks with the standard of LV Crystal Volume.
Figure 3B:
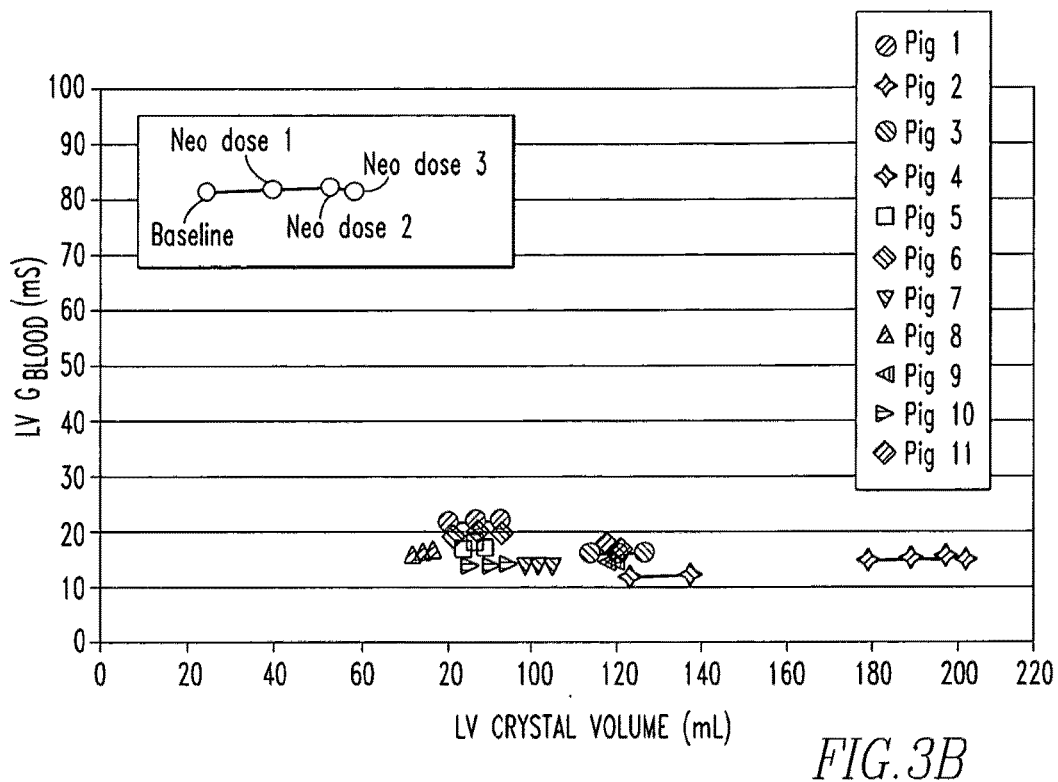
FIG. 3b shows the same data analyzed without subtracting the muscle component, demonstrating that dynamic removal of the myocardial signal using admittance is critical for detecting increasing LV Volume. The pig number is identified in the legend. There is variation in the absolute volumes in these hearts due to a large variation in porcine size.

Data from n=11 porcine studies is shown in FIG. 3. The low dose Neo was 90±54 µg/min, the high dose Neo was 180±107 µg/min. The blood conductance was computed from the epicardial impedance ($|\vec{Z}|$) and phase angle ($\angle \vec{Z}$), and plotted against LV volume calculated from endocardial crystals. LV end-diastolic volume (EDV) and complex impedance at end diastole were measured in each pig and the results were converted into the conductance of blood (LV $G_{blood}$) using the admittance technique, removing muscle contribution in real time (FIG. 3A). The conductance of blood ($G_{blood}$), expressed in milli-Siemens (mS), and LV volume (V), expressed in milliliters (mL), were measured at multiple values of LV volume for between 1 and 6 vectors on each pigs and the within-animal mean slope was computed for FIG. 3A. The slope relating $G_{blood}$ (mS) and the adjusted volume (mL), 1.16±0.48 mS/mL, was significantly different from zero (p=0.017). Data were also analyzed using the traditional conductance technique, which does not remove muscle contribution and demonstrates that the ability to detect LV dilation was lost and is dependent upon having access to the imaginary component of the myocardial signal (FIG. 3B).

LAD Occlusion for LV Dilatation

Hemodynamic parameters are shown in Table 1 at baseline and following LAD occlusion. Acute LAD occlusion produced a significant decrease in aortic pressure and flow. The anticipated increase in LV volume was detected by both the standard (endocardial crystals) as well as blood conductance. The large standard deviations in the blood conductance are a result of the wide range of electrode positions, and an offset, which may be caused by variable surface electrode-myocardium contact. On average, an increase of 17% from baseline LV blood conductance corresponded to an LV volume increase of 4%.

Transient Ao Occlusion

Hemodynamic parameters are shown in Table 2 at baseline and peak transient Ao occlusion. AoP and endocardial crystal derived LV volume both increase. Ao flow decreased below 1 L/min since that was the definition for a successful aortic occlusion. The increased afterload increases the LV blood conductance by 7%, and the crystal LV volume by 9%.

Pleural Effusion Simulation

Hemodynamic parameters are shown in Table 3 at baseline and pleural effusion simulation. Neither the LV blood conductance nor the crystal derived LV volume changed with saline placed around the heart 16.

This invention has demonstrated that LV blood conductance can be determined from the epicardial position, despite the current generating and sensing electrodes being in constant motion with the heart 16, and with dynamic removal of the myocardial component of the returning voltage signal. Specifically, it has been demonstrated that (a) a physiologic LV blood conductance signal can be derived, (b) LV dilation in response to dose-response iv Neosynephrine can be detected by blood conductance in a similar fashion to the standard of endocardial crystals when admittance is used, but not when only traditional conductance is used, (c) the physiologic impact of acute LAD occlusion can be detected by blood conductance as LV dilation, and (d) a pleural effusion simulated by placing saline outside the pericardium do not serve as a source of artifact for blood conductance measurements.

Pleural effusions are frequent findings in patients with advanced heart failure. Devices which interrogate the lungs for pulmonary edema use a trans-thoracic resistance measurement from the tip of the RV AICD lead to the case of the battery pack for the pacemaker/defibrillator, and thus provide a wide electric field including the LV, left atrium, thoracic skeletal muscle, ipsilateral lung tissue, intravascular blood volume in the lung, pulmonary interstitial edema and finally pleural effusions to measure a changing fluid index. Having an electrical approach that is focused on the LV myocardium and blood volume would be preferable, but there still exists some electrical field extension into other sources of artifact such as pleural effusions. To determine whether epicardial admittance would artifactually detect pleural effusions, fluid was placed outside the pericardium in the chest cavity to simulate this clinical condition. No alteration in the measurement of LV blood conductance was demonstrated in studies, arguing that epicardial admittance does indeed focus its interrogation on the LV itself.

The admittance technique (FIG. 3A) provides reliable tracking of LV preload similar to endocardial crystals, while traditional conductance does not (FIG. 3B). This increased sensitivity of the admittance technique is due to the use of a phase measurement in the calculation of the admittance, which allows the real-time separation of blood and muscle components. The high resistance of muscle normally swamps a measurement of blood and muscle in series, because the resistivity of muscle is nearly 5 times that of blood. This causes the total measured traditional conductance signal to be low and non-specific (FIG. 3B) when compared to the LV blood conductance determined using admittance (FIG. 3A).

In contradiction, studies by Stahl et al.[13, 15] using traditional conductance have shown promise in the detection of LV dilation using existing bi-ventricular leads. Stahl's invention is very different from the current invention for two reasons. The first major difference is that the stimulating electrodes span the LV, while in Stahl's they reside completely within the RV. In Stahl's design, the majority of current will be confined to the RV because the resistivity of muscle is 5 times higher than blood. This limitation is overcome in the current invention by forcing the current across the LV by maintaining the excitation and sink electrodes on opposite sides of the LV. The preferential path for current is therefore the low resistivity blood pool. The second major difference is that the current invention employs complex admittance for determining the relative muscle contribution to the measured signal. As seen in FIG. 3, this separation of blood from muscle provides increased sensitivity to heart failure detection (increasing LV preload). The present invention represents the first evidence that a cross-chamber complex admittance measurement shows improved sensitivity to LV blood pool volume measurement over a traditional conductance (or resistance) measurement.

In summary, a new electrical approach has been developed which can detect LV volume, taking advantage of pre-existing AICD and bi-ventricular pacing lead locations, and maturing the conductance approach to moving source and sensing electrodes while instantaneously removing the myocardial component to generate a final LV blood conductance signal.

References, all of which are incorporated by reference herein.

[1] Bleumink G S, Knetsch A M, Sturkenboom M C, Straus S M, Hofman A, Deckers J W, Witteman J C, Stricker B H: Quantifying the heart failure epidemic: prevalence, incidence rate, lifetime risk and prognosis of heart failure The Rotterdam Study. Eur Heart J 2004; 25:1614-1619.

[2] Bardy G H, Lee K L, Mark D B, Poole J E, Packer D L, Boineau R, Domanski M, Troutman C, Anderson J, Johnson G, McNulty S E, Clapp-Channing N, Davidson-Ray L D, Fraulo E S, Fishbein D P, Luceri R M, Ip J H: Amiodarone or an implantable cardioverter-defibrillator for congestive heart failure. N Engl J Med 2005; 352: 225-237.

[3] Bristow M R, Saxon L A, Boehmer J, Krueger S, Kass D A, De Marco T, Carson P, DiCarlo L, DeMets D, White B G, DeVries D W, Feldman A M: Cardiac-resynchronization therapy with or without an implantable defibrillator in advanced chronic heart failure. N Engl J Med 2004; 350:2140-2150.

[4] Cleland J G, Daubert J C, Erdmann E, Freemantle N, Gras D, Kappenberger L, Tavazzi L: The effect of cardiac resynchronization on morbidity and mortality in heart failure. N Engl J Med 2005; 352:1539-1549.

[5] Moss A J, Zareba W, Hall W J, Klein H, Wilber D J, Cannom D S, Daubert J P, Higgins S L, Brown M W, Andrews M L: Prophylactic implantation of a defibrillator in patients with myocardial infarction and reduced ejection fraction. N Engl J Med 2002; 346:877-883.

[6] Adamson P B, Magalski A, Braunschweig F, Bohm M, Reynolds D, Steinhaus D, Luby A, Linde C, Ryden L, Cremers B, Takle T, Bennett T: Ongoing right ventricular hemodynamics in heart failure: clinical value of measurements derived from an implantable monitoring system. J Am Coll Cardiol 2003; 41:565-571.

[7] Cleland J G, Coletta A P, Clark A L, Velavan P, Ingle L: Clinical trials update from the European Society of Cardiology Heart Failure meeting and the American College of Cardiology: darbepoetin alfa study, ECHOS, and ASCOT-BPLA. Eur J Heart Fail 2005; 7:937-939.

[8] Luthje L, Drescher T, Zenker D, Vollmann D: Detection of heart failure decompensation using intrathoracic impedance monitoring by a triple-chamber implantable defibrillator. Heart Rhythm 2005; 2:997-999.

[9] Magalski A, Adamson P, Gadler F, Boehm M, Steinhaus D, Reynolds D, Vlach K, Linde C, Cremers B, Sparks B, Bennett T: Continuous ambulatory right heart pressure measurements with an implantable hemodynamic monitor: a multicenter, 12-month follow-up study of patients with chronic heart failure. J Card Fail 2002; 8:63-70.

[10] Rozenman Y, Schwartz R S, Shah H, Parikh K H: Wireless acoustic communication with a miniature pressure sensor in the pulmonary artery for disease surveillance and therapy of patients with congestive heart failure. J Am Coll Cardiol 2007; 49:784-789.

[11] Vollmann D, Nagele H, Schauerte P, Wiegand U, Butter C, Zanotto G, Quesada A, Guthmann A, Hill M R, Lamp B: Clinical utility of intrathoracic impedance monitoring to alert patients with an implanted device of deteriorating chronic heart failure. Eur Heart J 2007; 28:1835-1840.

[12] Wang L, Lahtinen S, Lentz L, Rakow N, Kaszas C, Ruetz L, Stylos L, Olson W H: Feasibility of using an implantable system to measure thoracic congestion in an ambulatory chronic heart failure canine model. Pacing Clin Electrophysiol 2005; 28:404-411.

[13] Stahl C, Beierlein W, Walker T, Straub A, Nagy Z, Knubben K, Greiner T O, Lippert M, Czygan G, Paule S, Schweika O, Kuhlkamp V: Intracardiac impedance monitors hemodynamic deterioration in a chronic heart failure pig model. J Cardiovasc Electrophysiol 2007; 18:985-990.

[14] Yu C M, Wang L, Chau E, Chan R H, Kong S L, Tang M O, Christensen J, Stadler R W, Lau C P: Intrathoracic impedance monitoring in patients with heart failure: correlation with fluid status and feasibility of early warning preceding hospitalization. Circulation 2005; 112:841-848.

[15] Stahl C, Walker T, Straub A, Kettering K, Knubben K, Greiner T O, Paule S, Lippert M, Czygan G, Schweika O, Kuhlkamp V: Assessing acute ventricular volume changes by intracardiac impedance in a chronic heart failure animal model. Pacing Clin Electrophysiol 2009; 32:1395-1401.

[16] Feldman M D, Erikson J M, Mao Y, Korcarz C E, Lang R M, Freeman G L: Validation of a mouse conductance system to determine LV volume: comparison to echocardiography and crystals. Am J Physiol Heart Circ Physiol 2000; 279:H1698-1707.

[17] Porterfield J E, Kottam A T, Raghavan K, Escobedo D, Jenkins J T, Larson E R, Trevino R J, Valvano J W, Pearce J A, Feldman M D: Dynamic Correction for Parallel Conductance, GP, and Gain Factor, (alpha), in Invasive Murine Left Ventricular Volume Measurements. J Appl Physiol 2009.

[18] Raghavan K, Kottam A T, Valvano J W, Pearce J A: Design of a wireless telemetric backpack device for real-time in vivo measurement of pressure-volume loops in conscious ambulatory rats. Conf Proc IEEE Eng Med Biol Soc 2008; 2008:993-996.

[19] Raghavan K, Porterfield J E, Kottam A T, Feldman M D, Escobedo D, Valvano J W, Pearce J A: Electrical conductivity and permittivity of murine myocardium. IEEE Trans Biomed Eng 2009; 56:2044-2053.

[20] Reyes M, Steinhelper M E, Alvarez J A, Escobedo D, Pearce J, Valvano J W, Pollock B H, Wei C L, Kottam A, Altman D, Bailey S, Thomsen S, Lee S, Colston J T, Oh J H, Freeman G L, Feldman M D: Impact of physiological variables and genetic background on myocardial frequency-resistivity relations in the intact beating murine heart. Am J Physiol Heart Circ Physiol 2006; 291:H1659-1669.

[21] Wei C L, Valvano J W, Feldman M D, Nahrendorf M, Peshock R, Pearce J A: Volume catheter parallel conductance varies between end-systole and end-diastole. Ieee Transactions on Biomedical Engineering 2007; 54:1480-1489.

[22] Wei C L, Valvano J W, Feldman M D, Pearce J A: Nonlinear conductance-volume relationship for murine conductance catheter measurement system. Ieee Transactions on Biomedical Engineering 2005; 52:1654-1661.

[23] Baan J, Jong T T, Kerkhof P L, Moene R J, van Dijk A D, van der Velde E T, Koops J: Continuous stroke volume and cardiac output from intra-ventricular dimensions obtained with impedance catheter. Cardiovasc Res 1981; 15:328-334.

[24] Faes T J, van der Meij H A, de Munck J C, Heethaar R M: The electric resistivity of human tissues (100 Hz-10 MHz): a meta-analysis of review studies. Physiol Meas 1999; 20:R1-10.

[25] Steendijk P, van der Velde E T, Baan J: Dependence of anisotropic myocardial electrical resistivity on cardiac phase and excitation frequency. Basic Res Cardiol 1994; 89:411-426.

[26] Gaynor J W, Feneley M P, Gall S A, Jr., Maier G W, Kisslo J A, Davis J W, Rankin J S, Glower D D, Jr.: Measurement of left ventricular volume in normal and volume-overloaded canine hearts. Am J Physiol 1994; 266:H329-340.

[27] Graham M R, Warrian R K, Girling L G, Doiron L, Lefevre G R, Cheang M, Mutch W A: Fractal or biologically variable delivery of cardioplegic solution prevents diastolic dysfunction after cardiopulmonary bypass. J Thorac Cardiovasc Surg 2002; 123:63-71.

[28] Lainchbury J G, Meyer D M, Jougasaki M, Burnett J C, Jr., Redfield M M: Effects of adrenomedullin on load and myocardial performance in normal and heart-failure dogs. Am J Physiol Heart Circ Physiol 2000; 279:H1000-1006.

[29] Raghavan K, Wei C L, Kottam A, Altman D G, Fernandez D J, Reyes M, Valvano J W, Feldman M D, Pearce J A: Design of instrumentation and data-acquisition system for complex admittance measurement. Biomed Sci Instrum 2004; 40:453-457.

[30] Bourge R C, Abraham W T, Adamson P B, Aaron M F, Aranda J M, Jr., Magalski A, Zile M R, Smith A L, Smart F W, O'Shaughnessy M A, Jessup M L, Sparks B, Naftel D L, Stevenson L W: Randomized controlled trial of an implantable continuous hemodynamic monitor in patients with advanced heart failure: the COMPASS-HF study. J Am Coll Cardiol 2008; 51:1073-1079.

[31] Braunwald E: Braunwald's Heart Disease. A Textbook of Cardiovascular Medicine Saunders (Elsevier), 2005, pp. 540.
[32] Baan J, Jong T T A, Kerkhof P L M, Moene R J, Vandijk A D, Vandervelde E T, Koops J: Continuous Stroke Volume and Cardiac-Output from Intraventricular Dimensions Obtained with Impedance Catheter. Cardiovascular Research 1981; 15:328-334.
[33] Baan J, Vandervelde E T, Debruin H G, Smeenk G J, Koops J, Vandijk A D, Temmerman D, Senden J, Buis B: Continuous Measurement of Left-Ventricular Volume in Animals and Humans by Conductance Catheter. Circulation 1984; 70:812-823.

Tables

TABLE 1

LAD Occlusion.

|  | Baseline | Occlusion |
|---|---|---|
| HR (bpm) | 88 ± 19 | 87 ± 20 |
| AoP (mmHg) | 88 ± 9 | 83 ± 11 ‡ |
| Crystal Vol (mL) | 88 ± 12 | 91 ± 12 ‡ |
| Ao Flow (L/min) | 7.0 ± 1.3 | 6.4 ± 1.3 ‡ |
| RVSP (mmHg) | 24.5 ± 3.9 | 23.7 ± 5 |
| $G_{blood}$ (mS) | 73.6 ± 39.8 | 85.0 ± 51.1 ‡ |

Data from n = 6 pigs with 13 electrode positions are shown.
HR is heart rate, Aop is systolic right carotid pressure, Crystal Vol is 2D endocardial crystal LV volume, Ao Flow is descending thoracic aortic flow, RVSP is right ventricular systolic pressure, and $G_{blood}$ is LV blood conductance derived from epicardial admittance.
‡ p < 0.01

TABLE 2

Transient Aortic Occlusion.

|  | Baseline | Occlusion |
|---|---|---|
| HR (bpm) | 90 ± 28 | 97 ± 24 |
| AoP (mmHg) | 86 ± 11 | 124 ± 18 ‡ |
| Crystal Vol (mL) | 89 ± 21 | 98 ± 22 ‡ |
| Ao Flow (L/min) | 6.3 ± 1.2 | 0.7 ± 0.6 ‡ |
| RVSP (mmHg) | 22.9 ± 4.4 | 23.8 ± 4.4 ‡ |
| $G_{blood}$ (mS) | 53.5 ± 18.6 | 57.4 ± 21.6 ‡ |

Data from n = 11 pigs from 27 electrode positions are shown.
Occlusion data were defined at the time of peak AoP.
HR is heart rate, Aop is systolic right caotid pressure, Crystal Vol is 2D endocardial crystal LV volume, Ao Flow is descending thoracic aortic flow, RVSP is right ventricular systlic pressure, and $G_{blood}$ is LV blood conductance derived from epicardial admittance.
‡ p < 0.01

TABLE 3

Pleural Effusion Simulation.

|  | Baseline | Pleural Effusion |
|---|---|---|
| HR (bpm) | 95 ± 19 | 96 ± 21 † |
| AoP (mmHg) | 87 ± 5 | 86 ± 6 ‡ |
| Crystal Vol (mL) | 100 ± 29 | 100 ± 27 |
| $G_{blood}$ (mS) | 53.2 ± 33.5 | 52.6 ± 27.8 |

Data from n = 7 pigs from 54 electrode positions are shown.
HR is heart rate, Aop is systolic right carotid pressure, Crystal Vol is 2D endocardial crystal LV volume, and $G_{blood}$ is LV blood conductance derived from epicardial admittance.
† p < 0.05, ‡ p < 0.01

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. An apparatus for treating a heart of a patient comprising:
a pacemaker enclosure having:
a first existing lead and at least a second existing lead for pacing the heart adapted to be in electrical communication with the heart;
a microcontroller in communication with the first and second leads which triggers the first lead as a function of epicardial admittance in real time at either different times or a same time from when the microcontroller triggers the second lead for pacing the heart and takes into account delay between atrial pacing and ventricular pacing, where the admittance is a combination of both muscle and blood conductance and muscle susceptance components, where the blood and muscle components are in series and the admittance has both a real part and an imaginary part;
a pacing circuit in communication with the microcontroller which receives a signal from the microcontroller to activate the pacing circuit to control when the first lead and the second lead are activated to pace the heart; and
an admittance circuit which measures volume regarding the heart in real time in communication with the microcontroller, the microcontroller controls when the admittance circuit measures volume, the microcontroller determines from the admittance circuit in real time whether stroke volume, ejection fraction and end-systolic volume regarding the heart are increasing or decreasing over time, and changes the pacing circuit's operation in real time from the admittance circuit by cycling through pacing algorithms and changing a pacing algorithm which is used by the microcontroller, the microcontroller to maximize the stroke volume and ejection fraction and to minimize the end-systolic volume.

2. The apparatus of claim 1 including a pacemaker enclosure and wherein the admittance circuit is disposed in the pacemaker enclosure.

3. The apparatus of claim 2 wherein the microcontroller is disposed in the enclosure and including a wireless transmitter disposed in the enclosure which transmits a condition signal indicating whether the heart's condition is getting worse, better, or is without change.

4. The apparatus of claim 3 wherein the pacing circuit paces each ventricle of the heart separately, where each ventricle is paced separately using a variable time delay between a first and a second pace, or takes into account delay between atrial pacing and ventricular pacing, or a combination thereof.

5. The apparatus of claim 4 including at least a third lead for multiple admittance measurements adapted to be in electrical communication with the heart.

6. A method for treating a heart of a patient comprising the steps of:
receiving by a pacing circuit in a pacemaker enclosure in communication with a microcontroller in the pacemaker enclosure a signal from the microcontroller to activate the pacing circuit to control when a first existing lead and a second existing lead of the pacemaker enclosure is activated to pace the heart;
triggering with the microcontroller the first lead in electrical communication with the heart at various times for pacing the heart as a function of epicardial admittance in real time and takes into account delay between atrial pacing and ventricular pacing, where the admittance is a combination of both muscle and blood conductance and muscle susceptance components, where the blood and muscle components are in series and the admittance has both a real part and an imaginary part;

triggering with the microcontroller the second lead in electrical communication with the heart at different times than the various times for pacing the heart so that the microcontroller triggers the first lead at different times from when the microcontroller triggers the second lead; and measuring with an admittance circuit volume regarding the heart in real time in communication with the microcontroller, the microcontroller controlling when the admittance circuit measures volume, the microcontroller determining from the admittance circuit in real time whether stroke volume, ejection fraction and end-systolic volume regarding the heart are increasing or decreasing over time, and changing the pacing circuit's operation in real time from the admittance circuit by cycling through pacing algorithms and changing a pacing algorithm which is used by the microcontroller, the microcontroller to maximize the stroke volume and ejection fraction and to minimize the end-systolic volume.

7. The method of claim 6 including the step of determining stroke volume, and systolic volume, and ejection fraction of the heart using epicardial admittance.

8. The method of claim 7 including the step of pacing the heart by separately pacing each ventricle of the heart using a variable time delay between a first and a second pace, or by taking into account delay between atrial pacing and ventricular pacing, or by a combination thereof.

9. The method of claim 8 including the step of re-measuring stroke volume, and systolic volume, and ejection fraction after changing how the heart is paced.

10. The method of claim 9 including the step of comparing the determining step and the re-measuring step, and repeating them until the stroke volume and ejection fraction are maximal, and end-systolic volume is minimal.

* * * * *